Figure 1:
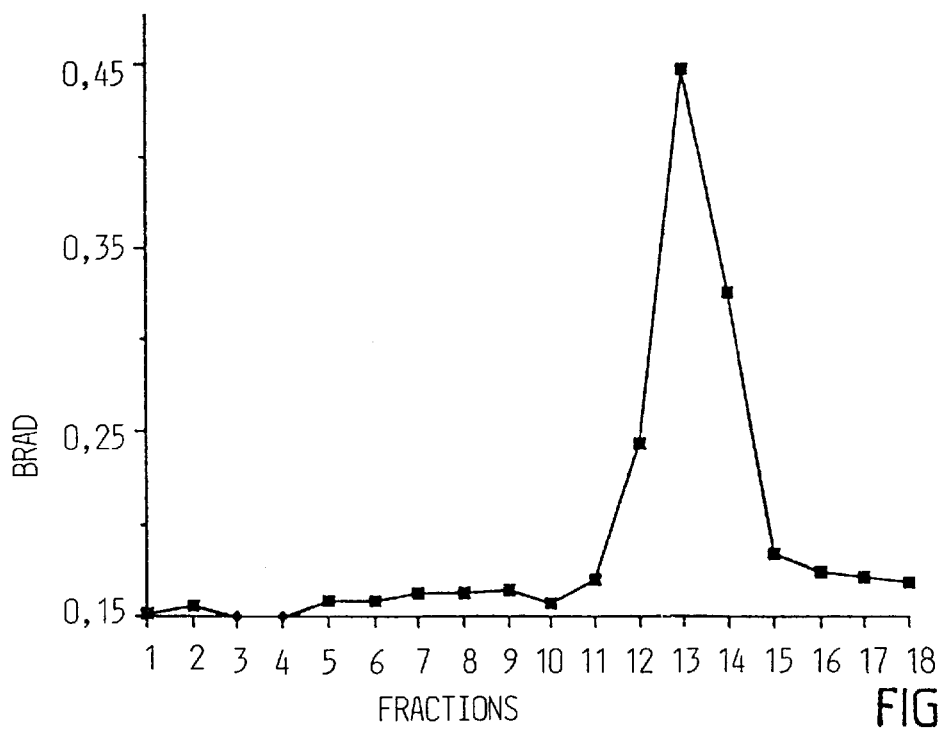

United States Patent [19]
Morein et al.

[11] Patent Number: 6,027,732
[45] Date of Patent: Feb. 22, 2000

[54] ISCOM OR ISCOM-MATRIX COMPRISING HYDROPHOBIC RECEPTOR MOLECULES FOR ANTIGENIC SUBSTANCES

[76] Inventors: Bror Morein, Ollonstigen 3, Vreta, S-755 90 Uppsala; Karin Lovgren Bengtsson, Hojdvagen 30 A, S-756 53 Uppsala; Jill Ekstrom, Klev, S-741 91 Alunda, all of Sweden

[21] Appl. No.: 09/125,588

[22] PCT Filed: Feb. 20, 1997

[86] PCT No.: PCT/SE97/00287

§ 371 Date: Sep. 17, 1998

§ 102(e) Date: Sep. 17, 1998

[87] PCT Pub. No.: WO97/30726

PCT Pub. Date: Aug. 28, 1997

[51] Int. Cl.$^7$ .................. A61K 39/108; A61K 39/00; A61K 39/38; A61K 39/02; A61K 45/00
[52] U.S. Cl. .................... 424/241.1; 424/241.1; 424/184.1; 424/234.1; 424/236.1; 424/278.1; 424/422; 424/489; 536/4.1; 536/5; 536/6.3
[58] Field of Search ................ 424/422, 278.1, 424/241.1, 184.1, 234.1, 236.1, 489; 536/41, 5, 6.3

[56] References Cited

U.S. PATENT DOCUMENTS

| | | |
|---|---|---|
| 4,303,638 | 12/1981 | Tayot et al. . |
| 5,178,860 | 1/1993 | MacKenzie . |
| 5,620,690 | 4/1997 | Kersten et al. . |

OTHER PUBLICATIONS

K. Scheepers et al., "Protection of Mice Against an Influenza Virus Infection by Oral Vaccination with Viral Nucleoprotein Incorporated into Immunostimulating Complexes", Medical Microbiology and Immunology, (1994) 183: pp. 265–278.

M. Hazama et al., "Intranasal Immunization Against Herpes Simplex Virus Infection By Using a Recombinant Glycoprotein D Fused with Immunomodulating Proteins, the B Subunit of *Escherichia coli* Heat–labile Enterotoxin and Interleukin–2", Immunology 1993, 78, pp. 643–649.

Carl R. Alving et al., "Effectivenee of Liposomes as Potential Carriers of Vaccines: Applications to Cholera Toxin and Human Malaria Sporozite Antigen", Vaccine, vol. 4, Sep. 1996, pp. 166–172.

Jan Holmgren et al., "Cholera Toxin and Cholera B Subunit as Oral–Mucosal Adjuvant and Antigen Vectors Systems", Vaccine, vol. 11, Issue 12, 1993, pp. 1179–1184.

Jim Vadolas et al., "Intranasal Immunization with Liposomes Induces Strong Mucosal Immune Responses in Mice", Eur. J. Immunol. 1995, 25: pp. 969–975.

Nabila M. Wassef et al. "Prostaglandin and Thromboxane in Liposomes: Suppression of the Primary Immune Response to Liposomal Antigens", Biochemical and Biophysical Research Communications, vol. 160, No. 2, Apr. 1989, pp. 565–572.

Friedhelm Helling et al., "$G_{D3}$ Vaccines for Melanoma: Superior Immunogenicity of Keyhole Limpet Hemocyanin Conjugate Vaccines[1] ", Cancer Research 54, Jan. 1994, pp. 197–203.

Alan J. Husband, "Novel Vaccination Strategies for the Control of Mucosal Infection", Vaccine, vol. 11, Issue 2, 1993, pp. 107–112.

*Primary Examiner*—Nita Minnifield
*Assistant Examiner*—Padma Baskar
*Attorney, Agent, or Firm*—Young & Thompson

[57] ABSTRACT

Lipid-containing particles such as iscoms, iscom-matrix or vesicles such as micelles or liposomes that comprise one or more hydrophobic receptor molecules for targeting and antigenic substances, which receptor molecules have been integrated in the particle and are chosen from lipid-containing receptors or receptors that are hydrophobic, which receptor molecules bind to the antigenic substances.

10 Claims, 6 Drawing Sheets

ISCOM OR ISCOM-MATRIX COMPRISING HYDROPHOBIC RECEPTOR MOLECULES FOR ANTIGENIC SUBSTANCES

The invention involves lipid-containing particles, chosen from iscoms and iscom matrices, which contain one (several) hydrophobic receptor component(s) which bind to antigens from microorganisms such as bacteria, virus, or parts thereof, i e the receptor-binding parts, such as toxins or surface proteins.

Furthermore, the invention involves procedures for producing such lipid-containing particles and the human medical, veterinary medical, or other pharmacological preventive and curative use, such as immunotherapeutic, of these particles. The invention involves in particular iscoms and iscom matrices whose surfaces have been prepared with bacterial toxin fragments such as the cholera toxin's B subunit (CTB).

THE BACKGROUND OF THE INVENTION

Lipid-containing structures in the form of micelles, liposomes and other visicles, iscoms (immune-stimulating complex/particles), iscom matrices, etc. have been reported as effective carriers of pharmacologically and/or immunologically active substances or molecule complexes. See for example WO-A1-90/03184 (Morein et. al., Clin. Immunother. Review, 1995; Kersten et. al., Iscom—Liposome Review, 1995). In many cases, immunization of laboratory animals with such lipid-containing structures, in which various antigens have been incorporated, have been shown to give rise to an increased immune response to the referred antigens as compared to the immune response obtained after immunization using a corresponding antigen in a free form.

Iscom and iscom matrices are documented as effective carriers of antigens and adjuvant molecules to enhance the immunogenicity of small and large molecules (antigens), i e to make them strongly immunogenic both when they are applied parenterally and locally, (topically) on mucous surfaces. The iscom has unique properties being effective after mucosal intranasal adminstration. It is well-documented (Morein et. al., Clin. Immunother. 3, 1995, 461–475) that both iscoms with incorporated antigens (usually protein) and iscoms as carriers, for example small antigens such as oligopeptides or as exemplified by biotin, effectively evoke immune response to these large or small molecules.

Iscom matrices (and iscom) have well-documented, built-in, adjuvant activity that potentiates antibody-mediated as well as cell-mediated immune responses to the co-administered antigens. Iscom evokes cell-mediated immune response under both Class I and Class II restriction.

Cholera is the most serious of all the diarrhea diseases and is caused by the Vibrio cholera bacteria in group 1. These bacteria colonize in the small intenstine of human beings and secrete an exotoxin protein known as the cholera toxin. This toxin binds to and is absorbed by cells in the mucous membranes and causes an intensive secretion of electrolytes and water from the cells, which leads to the grave cases of diarrhea, dehydration, and metabolic acidosis which characterize cholera.

Similar diseases can be caused by so-called "enterotoxic" (ET) cholibacteria, but the symptoms are usually milder. Such bacteria often cause diarrhea in young individuals among humans and practically all kinds of animals, including pigs and cattle. These diarrheas, which can give rise to great economic losses for the livestock industry, are caused partly by a heat-labile toxin (LT) similar to the cholera toxin (CT). These toxins are so similar that they bind to the same receptors.

The structures of CT and LT are well defined in regards to structure and function. They are oligomeric proteins consisting of one part that binds to the cholera toxin receptor, namely the B part, which in turn consists of five subunits which each have an approximate mole weight of 11,600 and form a pentamer ring. The A subunit is a proteolytic split polypeptide with a molecular weight of approximately 28,000, consisting of two disulfid-conjugated fragments. The larger A1 fragment contains toxin-enzyme activity, while the smaller A2 fragment joins the A1 fragment with the B5 ring. CT binds with high affinity to a class of receptors that exist on the surface of the so-called brush-border membranes in the small intestine, as well as to the plasma membrane of most mammalian cells. The GM1 gangliosid constitute the receptor for CT (Holmgren et. al., Infect. Immun. 38, 424–433). LT also binds to GM1.

CT and LT, respectively, are both important components in the subunit vaccines that are intended to evoke protection gains cholera and enterotoxic cholibacteria. In the case of intestinal infections, it is of special interest to evoke local protection exerted by, among other things, secretory IgA in the intestinal membrane. CT and LT are both considered well suited as targeting molecules in adjuvant formulations for vaccines intended for adminstration in the intestinal and respiratory tracts (Morein. Lövgren and Cox, 1966), with, among other things, having the capacity to induce a secretory IgA response that is an important component in the protection. The B subunit of CT and LT have attracted a good deal of interest as carrier molecules and even as universal vector systems for oral vaccines (Mucosal Handbook Immunology, eds Ogra, P. L., Lamm Me, Mc Ghee Jr., Mestechy J., Strober W. Bienenstock J., 1994). The interest has increased even more because it has been shown that the conjugate between CTB and other antigens not only give rise to immune response in the local intestinal mucosal membranes, but also to a limited extent in other remote mucous membranes, such as the salivary glands, the lungs, the genital tract, and in the blood (Handbook mucosal, 1994). The problem with CTB and LTB is that they have a low (inate)-capacity to potentiate their own strong, protective immune response against the cholera toxin or against LT, or against the antigen that they are modified to be a carrier for. They thus have a low adjuvant activity in relation to the immunomodulatory and immunopotentiating effect (Morein, Lövgren and Cox, 1966).

CTB and LTB are used experimentally as carriers of antigen with the purpose of evoking, through local application (orally), local immune response in the mucous membranes of the digestive tract as well as in other mucous membranes through gut-associated lymphatic traffic (GALT) or through direct application on other mucous membranes such as the respiratory tract. CTB and LTB have targeting capacity, which means that they are considered to steer and localize both themselves and the antigens they may carry to the lymphatic system in the intestinal tract, which means to M-cells in Payer's patches, to lamina propria (LP), and to the lymphatic system in the intestines and in other mucous membranes through GALT or through direct application on these mucous membranes, for example in the respiratory tract.

The following unsolved difficulties exist regarding using CTB and LTB for local immunization:

1. CTB and LTB have by their own relatively low immunogenicity and a low immunoenhancing capacity, requiring a need to be potentiated with an adjuvant component to obtain optimal effect. In other words, this involves both their own immunogenicity and their immunoenhancing effect to the antigens that they may have carried with them. Their value as adjuvants is limited to "targeting", while supplementary adjuvant activities in the form of immunomodulatory and immunoenhancing capacities are required in order to attain optimal immunogenicity.

2. There are limitations to conjugating antigens to CTB and LTB with particularly high physical or economic yield, since only a limited number of amino groups and/or carboxy groups can be activated without seriously reducing their values as antigen or as carriers in mucous membranes, and target themselves and the accompanying antigens to the lymphatic organs and cells to evoke immune response. Even if a sufficient number of coupling groups are available on a carrier molecule, it is well known that it is difficult to attain the desired economic yield from such constructions because of the insufficient yield. For example, often no more than 15–20% of the available antigens are coupled in reaction to the carrier molecule.

3. CTB and LTB have a limited space for chemically coupling of larger molecules, because they can block functional epitopes that are necessary for targeting the complexes to the lymphatic organs and cells.

SUMMARY OF THE INVENTION

It has now been demonstrated that through the use of lipid-containing particles, chosen from iscoms and iscom matrices or micelles or vesicles like liposomes that contain one or more hydrophobic receptor molecules for antigen substances or targeting molecules, a contribution is made toward a new, general system for binding molecules. These receptors can be lipid-containing receptors or receptors that are hydrophobic proteins. Through this new, general system, a greater proportion of antigens or other substances are bound to the particle, with a yield that begins to approach 100%, which is economically advantageous, but above all the new system makes it possible, without competition from earlier systems (that do not use the receptor) (EP 0 109 924 B1, EP 0 180 546 B1, EP 0 242 380 B1), to bind in antigen and targeting molecules or molecule complexes. Consequently, the immune response is more efficiently induced by the antigens that are bound to the receptor. Above all, it becomes possible to bind antigen to the receptor together with the other antigens that are incorporated without using the receptor. With this invention it is easier to bind both targeting molecules which can, for example, penetrate mucous membranes, and passenger antigens which cannot be absorbed by mucous membranes (see the Swedish patent application 9600647-3). A special advantage is that lipid-containing receptors can be used as an integrated lipid in the complexes, that is, they can replace lipids that are used to build up the complex (pat. lipid Iscom).

Among the receptor-binding components that are comprised by the invention are, for example, bacterial toxins and their active binding parts in the form of subunits or fragments or various modifications or derivatives of them, bacterial fimbriae or other adhesion molecules and their active binding parts and/or derivative structures. In many cases these targeting structures are also relevant vaccine antigens, and the presentation of such antigens on the surface of lipid-containing particles, etc., for vaccination use are also part of the invention.

Iscom contains at least one glycoside, at least one lipid, and at least one kind of antigen substance, particularly proteins and peptides. These complexes enhance the immunogenicity of the included antigens and may also contain one or more immunomodulatory (adjuvant-active) substances and are described in EP 0 109 924 B1, EP 0 242 380 B1 and EP 0 180 546 B1.

Matrix contains at least one glycoside, one adjuvant-active substance and at least one lipid. Matrix has an immunoenhancing effect on co-administered antigenic substances, see EP 0 436 620 B1.

It has been shown that the lipids in these complexes can be partly replaced by lipid-containing receptors for antigen substances from microorganisms. In this way, the amount of antigen that binds to the particle is appreciably increased.

In those cases where the complexes are iscoms, these iscoms are prepared as described in the European patent EP 0 109 942 B1. Here, virus, mycoplasma, bacteria, parasites, animal cells, containing antigens or antigenic determinants, especially proteins or peptides or isolated examples which have hydrophobic or amphiphatic regions, is mixed with one or more solubilizing agents, whereby complexes are formed between antigens or antigenic determinants and solubilizing agents, after which the antigens or determinants are separated from the solubilizing agent in the presence of, or are separated from the solubilizing agent and directly transferred to, a glycoside solution, containing cholesterol, phospholipid, and one or more glycosides (Quillaja components) with hydrophobic and hydrophilic domains in a concentration of at least the critical micelle-binding concentration, whereby a protein complex is formed, which is then isolated and purified.

The lipids that are used are in particular those described in the applicant's patent EP 0 109 952 B1, especially on page 3, and in EP 0 436 620 B1, p. 7, lines 7–24. In particular, sterols such are cholesterol and phospholipids such as phosphatidyl-ethanolamine and phosphatidylcholine are used.

The lipids can also include lipophilic receptor molecules that bind to cell-binding components, especially antigens. Such receptors are glycolipids, for example the cholera toxin's receptor ganglioside GM1 and fucosylated blood group antigen. The cell-binding components can then function as transport molecules. They are bound to the lipid-containing receptor by a simple mixing with the complex that contains the receptor. Then the iscom or matrix molecule can be mixed with the antigen that binds to the receptor.

It is possible to proceed from matrix that can be made by solubilizing at least one sterole in a solution agent, adding the glycoside or the saponines and the other lipids, after which the solution agent may be removed, if it unacceptable to the final product. Matrix is usually transferred to a water solution in which its separate parts are not soluble. The solubilizing agent can be removed through eg gel filtration, ultra filtration, dialysis, or electrophores. The matrix can then be purified from surplus of sterole and saponine eg by ultracentrifugation, through a density gradient or through gel filtration. The solubilizing agent can be any of those mentioned in EP 0 436 629 B1, p 5 row 24–45. The other components and the procedure are also described in this document.

The glycosides that are used in the procedure can be those described in EP 0 109 942 B1 p 4 last paragraph. Especially saponines are used, such as triterpensaponines, especially Quillaja saponins from Quillaja saponaria Molina or cell cultures from this tree or subcomponenets thereof, especially those described in the applicant's European patent EP 0 436 620 B1 p 4 rows 19–46. These can be QHA, QHB, QHC, or other compositions of Quillaja saponins. The glycosides are adjuvants and structure-building elements in iscom and matrix. It is also possible to incorporate other adjuvants or immunomodulatory components than glycosides in the iscoms or in the matrices as is mentioned in EP 0 436 620 B1.

It is also possible to mix the transport molecule and/or the passenger antigen as a separate entity with an iscom particle in which the passenger antigen or the transport (targeting) molecule has been integrated, or with iscom and/or matrix complex on which the passenger antigen or the transport molecule has been coupled, ie many combination are possible. By definition, an iscom particle contains antigen and iscom-matrix lack antigen. Even other adjuvants or immunomodulatory components can be mixed with the iscom and/or matrix complexes as separate entities, ie they do not necessary have to be integrated in the complexes or coupled to these. Examples of such adjuvants are provided in Cox et. al., CRS, 1992. Usually, MDP, MTP, and avridin are used. It is however advantageous to incorporate these adjuvants in iscom and matrix when a lower dosage of adjuvants is required. It is also possible to mix both the transport molecule and the passenger antigen with iscom-complex or matrix. In these cases, the iscom complex contains another antigen molecule.

If the transport molecule(s) or passenger antigen(s) lacks hydrophobic or amphiphatic groups, they can be chemically coupled to the iscom particle. Examples of such coupling procedure and coupling groups are found in EP 0 242 380 B1 p 9 and in EP 0 426 620 B1 p 6 row 33-p 7 row 6, where the coupling method is also described. They can be lipids as in example 7 below.

The relative amounts of cholesterol, lipids and antigen that can be used can be found in the above-mentioned patents EP 0 109 942 B1, EP 0 180 564 B1, EP 0 242 380 B1 and EP 0 436 620 B1.

The lipid-containing receptors can also be included in other lipid structures such as liposomes, vesicles, micelles.

When the receptor is a hydrophobic protein such as a glycoprotein or a fucosylated blood group antigen, it can be integrated in the lipid molecule with a hydrophobic interaction. It can also be included in iscom as a protein share.

Besides the antigen that attach to the receptor, other antigens can be made to attach to the receptor through the substitution of appropriate groups. Such appropriate groups, which can be attached to such other antigens, can be parts of the antigen that attach to the receptor. These parts can be bound with familiar methods, for example those mentioned in EP 0 436 620 B1. It is also possible through gene-technological manipulation to construct fusion proteins or peptides between an antigen and parts of it and the receptor-binding antigen. Other antigens than those that come from cholera and enterotoxic cholibacteria can thereby be bound to the GM1 receptor by substitution with parts of the CTB or LTB. Examples of this are given in Biochemia et biophysica Acta 1223 (1994) 285–295 "Regeneration of active receptor recognition deomaisn on the B subunit of cholera toxin by formation of hybrids from chemicall inactivated derivatives". Marc J. S. De Wolf. Wilfried S. H. Dierick. In this way, antigens that do not normally penetrate a mucous membrane can be passed through the mucous membrane.

CTB is thereby a useful carrier for chemically and genetically produced antigens: Sanchez & Holmgren (Proc. Natl. Acad. Sci. USA, 86 481–485, 1989) and Sanchez, Johansson et al. (Res. Microbiol. 141, 971–979, 1990). With the aid of recombinant DNA techniques, foreign antigens have been bound to the antigen amino or carboxiy ends of the CTB subunit and a gene has been expressed that, via expression systems, has been developed to produce the hybrid protein.

In the examples described to illustrate the invention, iscom matrix such as lipid-containing particles and the cholera toxin B subunit (CTB) have been used as receptor-specific binding structures and as a relevant vaccine antigen.

The cholera toxin consists of an A subunit that exerts the toxin activity and the B subunits that attaches the toxin to the plasma membrane on the cell through a glycolipid (GM1). To reduce the toxicity, usually only the B subunit of the cholera toxin (CTB) is used as vaccine antigen to evoke immune response. The B subunit is not toxic and evokes a relatively weak immune response as compared to CT after local (mucosal) intranasal or systemic parenteral immunization, for example subcutaneous or intramuscular immunization, ie the B subunit has low adjuvant activity when the activity refers to immunomodulating or immuno enhancing activity. CTB is also available as a recombinant DNA product (rCTB) (EP 368 819).

It is difficult to couple antigen covalently to CTB or LTB with high physical and economic yields, since only a limited number of amino groups and/or carboxy groups can be activated without seriously reducing the antigenic activity of CTB and LTB or not to harm their capacity as carrier molecules in the mucous membranes, and to target themselves and accompanying antigens to lymphatic tissues and organs and cells to evoke immune response. Even if a sufficient number of groups are available for chemical conjugation of antigen(s) on a carrier molecule, it is well known that it is difficult to receive good and economic yields from such constructions (Lövgren, et al., J. Immunol. Methods 173.237–243).

The utilization of transport proteins in iscoms has several advantages. This is especially evident for construction of oral, nasal, or rectal vaccines against infections. Such vaccines can contain a carrier construction with antigen and adjuvant component(s), supplemented for example with CTB or LTB to localize the construction to lymphatic organs and cells in the intestinal tract and to target immune response to lymphatic tissues in other mucous membranes via GALT, MALT, NALT (Gut, Mucosal and Nasalfaryngial Associated Lymphatic Tissue, respectively), for example after administration in the respiratory tract or by direct local mucosal application.

The iscom is larger than transport molecules like CTB or LT and therefore there is room to conjugate or in some other way, for example through hydrophobic or electrostatic binding, to incorporate chosen passenger antigens and incorporate chosen adjuvant components.

In producing matrix, the weight ratio of sterol, second lipid, and glycoside is 0.2–10:0,2–10:1–100, preferably 1:1:5. If a lipid-containing receptor is used, it can replace the other lipid(s) completely so that the ratio of sterol, lipid-containing receptor, and glycoside will be as above. It is also possible to use both the lipid-containing receptor and a second lipid, preferably phosphatidylcholin or phosphatidyl ethanolamin and the receptor so that the ratio becomes sterol:second lipid:receptor:glycoside 0.2–10:0.2–10:0.1–1:5–10, preferably 1:1:0.25:5. The amount of receptor molecule depends on the amount of target or antigen molecules one wishes to add on.

The constitutents can, in principle, be put in any ratio whatsoever. It has been proven that the finished product obtains the preferred weight ratio between the included components and that the surplus does not enter. If a large amount of the second lipid, such as phospholipid, is used, the complex becomes fatty and fragile and easily falls apart. Too little of the second lipid makes it difficult for complex to be formed, and annularly ring-shaped subunits are formed. This can be determined by electron microscopy.

Figure 3:
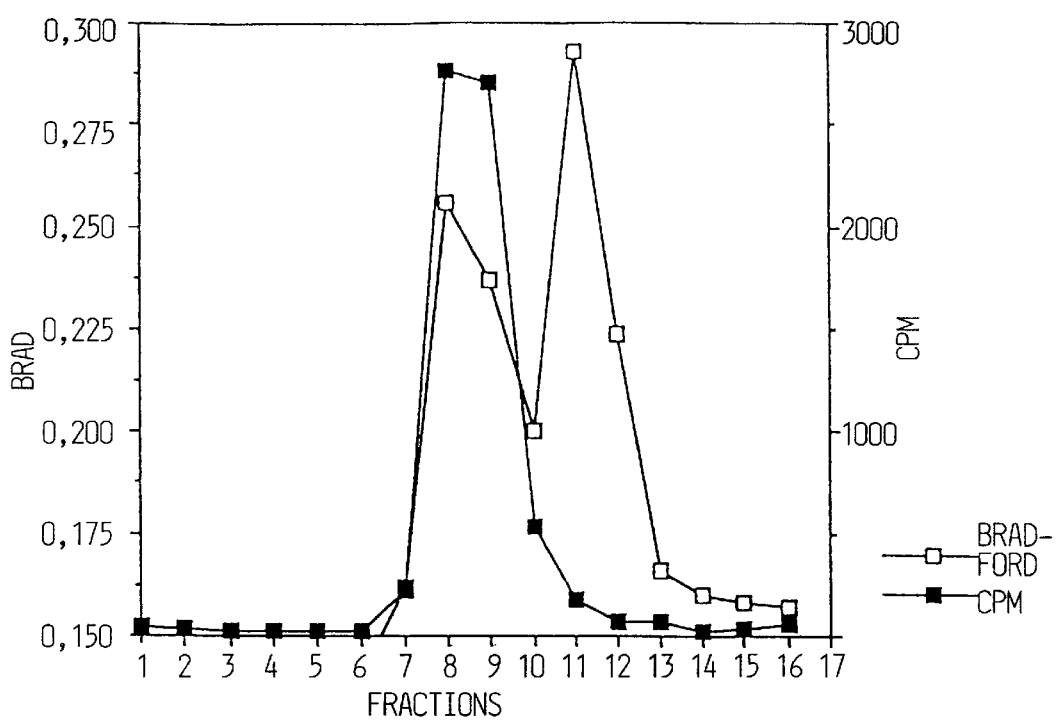

Whether iscom or matrix has been formed can be confirmed by studying the product by electron microscopy. Typical matrix or iscom have a characteristically open, spherical structure containing circular subunits or parts of the spherical structure, as can be seen in FIG. 3 in EP 0 109 942 B1. The iscoms have a lower sedimentation constant than the corresponding micelles and often a higher sedimentation constant than the corresponding monomeric forms of protein or peptide. Matrix and iscom have a sedimentation constant of approximately 20 S.

The advantage of using lipid-containing receptors for binding target-seeking or vaccine antigens is that it is possible to produce matrix from glycoside, sterol, possibly a second lipid, and a lipid-containing receptor and then simply mix the ready matrix with the transport (targeting) molecule. The procedure is cheaper and simpler than if one were to make ready-made iscom containing the ingredients above plus a transport antigen, or if one were to joint the antigen to ready-made matrix using chemical conjugation methods.

When the antigen is integrated into iscom or is coupled chemically to matrix, amino groups or carboxyl groups, which can constitute antigenic determinants, are modified. The antigenic determinants are denatured when the antigen is activated for integration in iscom or when it is coupled chemically to matrix or iscom (when two antigens are used, iscom already contains at least one antigen). This means that the active antigen amount is considerably reduced. Moreover, the recovery is low compared to when the antigen is allowed to bind to a lipid-containing receptor. This can mean for example that in the preparation process approximately five times more antigen is required as compared to when a lipid-containing receptor is used. When a lipid-containing receptor is used, the process is considerably cheaper. Parallel to reduced incorporation, the amount of glycoside and adjuvant content per unit of antigen is increased, which partly compensates the lower amount of antigen as regards the achieved immune response, but at the same time, toxicity can increase because of the increased percentage of adjuvant. The immune response, on the other hand, becomes higher in principle when using receptor-binding of the antigen, while the original conformational antigenic determinants are retained.

Another advantage presents itself when it is desirable to join a transport (targeting) molecule and a passenger antigen to iscom or matrix. If iscom or matrix has been made with lipid-containing receptors, there is more room for integrating passenger antigens in the iscom or for coupling it chemically to the matrix. By using lipid-containing receptor, the binding of the passenger antigen is not influenced. It becomes easier to reach optimal conditions. Control of the amount of passenger antigen or transport (targeting) molecules, integrated in iscom or linked chemically to iscom or matrix, is made better. If iscom is made with both a transport (targeting) molecule and an antigen using the same methods, they may compete for the binding regions and it is not possible to fully control the incorporations of the two antigens.

Especially in regard to the cholera antigen CTB, which has five binding subunit, it is possible to bind up to 13 times the weight amount of the GM1 receptor. There are still binding sites left in CTB, which can bind to cell receptors in the mucosa and serve as transport (targeting) molecules.

The weight ratio of sterol, second lipid, protein and glycoside is 0.2–10:0.2–10:0.2–10:1–100, preferably 1:1:1:5–10 to be used with subcutaneous administration. With oral or intranasal administration, the amount of glycoside can be higher in the ratio above, namely 1–200, preferably 5–20.

These amount apply both when first making matrix and then when chemically coupling the antigens and when making iscom particles.

The procedure for preparing CTB (or LTB) iscoms entails mixing Quil A or Quil A components with a lipid mix containing cholesterol, phosphatidylcholin and Gal 1–3, Gal NAcb 1–4 (Neu Aca2–3), gal(GM1), which is a specific receptor for the cholera toxin (CT) and the heat-labile toxin from enterotoxic $E.$ $coli$ (LT) as well as their subunits CTB and LTB. Phosphatidylcholin (PC) can wholly or partly be replaced with phosphatidylethanolamine (PE), whereby the amino group on PE constitutes a coupling group for antigen or other desired components. Unlike cholesterol, PC and PE are not essential to the iscom composition but can be replaced with other "soft" lipids.

Iscom or iscom matrix can be made in compositions containing a solubilizing agent such as water or physiological saline. For solubilizing agent, the composition can also include the detergent that the complex is made with if it is acceptable to human or veterinary medicine. The compositions can also include other additives and fillers acceptable to human or veterinary medicine.

Such a composition can contain for example iscom complex and a filler such as physiological saline. It can also be composed of matrices mixed with antigen. The vaccine can be made available in administrative forms that contain an entity with matrix in a composition containing a filler and a unit with the antigen in a composition containing a filler. Both of these compositions are then intended to be administered on the same occasion.

The amount of iscom, matrix and antigen is chosen so that it will be pharmaceutically effective and can be decided by the expert. For humans, at least 1 µg, preferably 1–200 µg of the antigens, should be used, whereby economic opinion sets the upper limit. For animals, the dosage can be at least 0.1 µg of the antigens, depending on the antigen and the individual's size.

All cited publications and the Swedish priority application 9600648-1 are incorporated herewith for reference.

SHORT DESCRIPTION OF THE FIGURES

FIG. 1 shows that free rCTB (recombinant CTB) analyzed in a 10 to 50% sucrose gradient after ultracentrifugation is located at the top on the gradient, ie fraction 12–14. Cf FIGS. 2 and 3.

Figure 2:
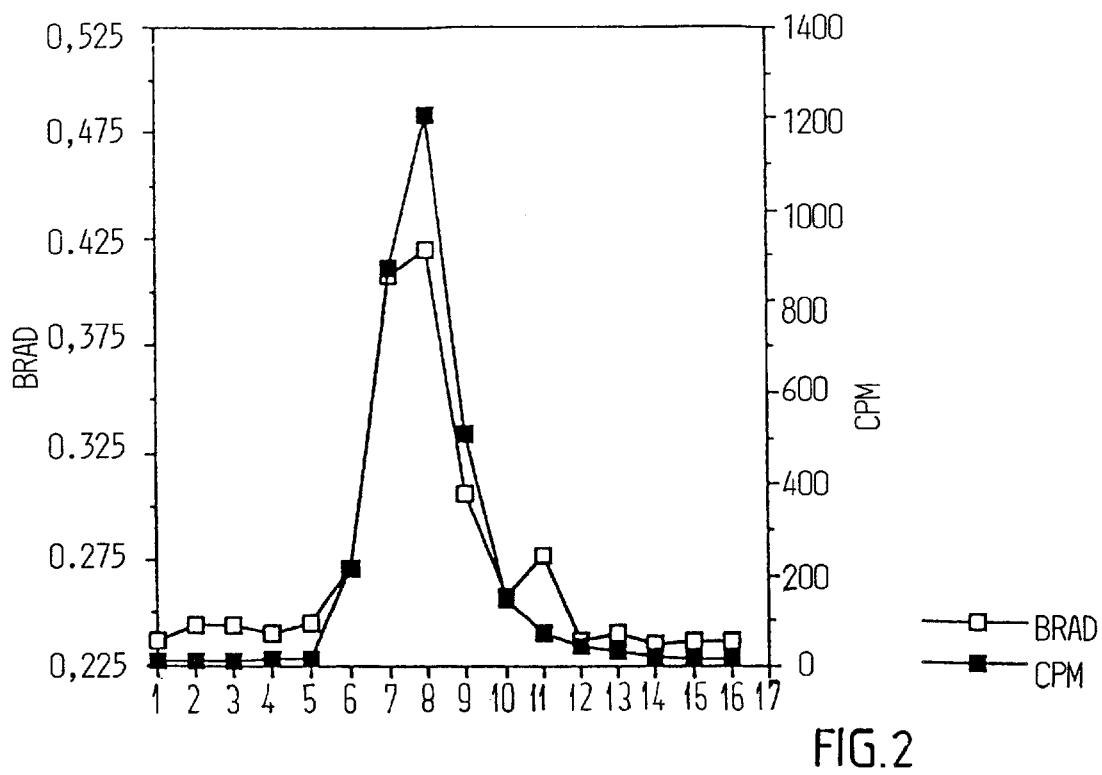

FIG. 2 shows iscoms with rCTB in a diagram where fractions in a 10–50% sucrose gradient after centrifugation are plotted against 1) the absorbency at 595 nm for determination of the rCTB concentration using the method Bradford, and 2) CPM from analysis of $^3$H cholesterol, an iscom-matrix component. Iscom matrix with rCTB and GM1 at the weight ratio 13:1 is made according to example 1 and is then ultracentrifuged. Iscoms with rCTB are found in the fractions 6–9. Nearly all rCTB are to be found in iscoms.

FIG. 3 shows a diagram of the same kind as FIG. 2. In making iscoms in this trial, the rCTB concentration was 100 times greater than the GM1 concentration w/w. Non-incorporated rCTB are to found in the upper Bradford top, that is, higher up in the gradient in the fractions 10–12.

Figure 4A:
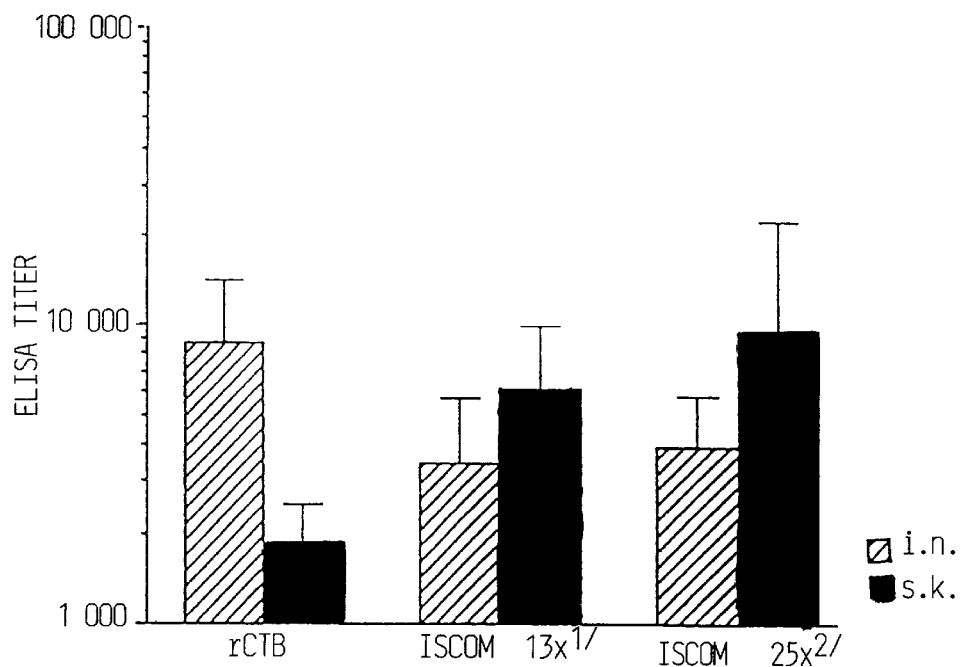
Figure 4B:
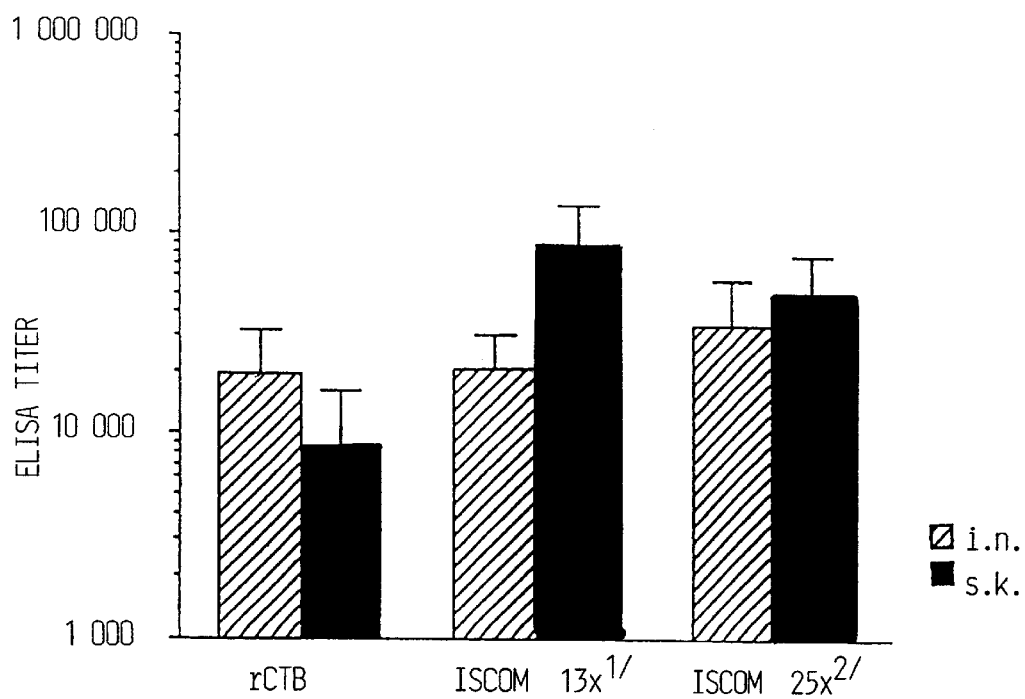

FIGS. 4A and 4B are bar graphs that show the ELISA titer in serum from mice after immunization with free rCTB and rCTB that has been incorporated in iscom matrix.

The solid bars refer to subcutaneous immunization while the diagonal bars refer to intranasal immunization. FIG. 4A shows serum antibody titers 5 weeks after the first immunization while FIG. 4B shows the titer 6 weeks after the second immunization. The interval between the immunizations was 6 weeks.

Figure 5A:
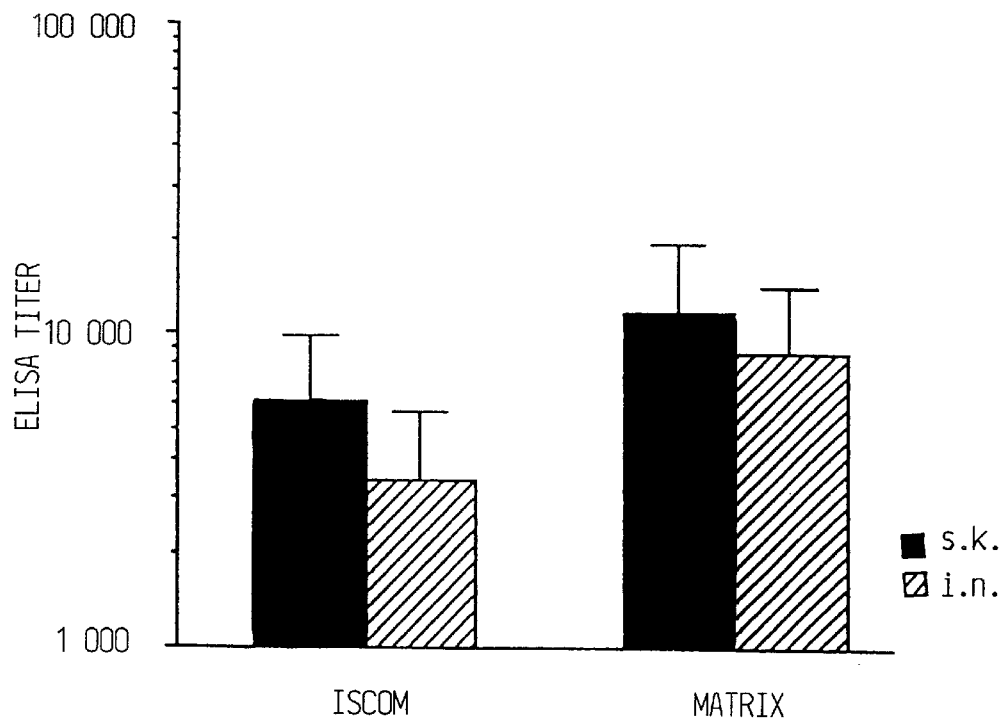
Figure 5B:
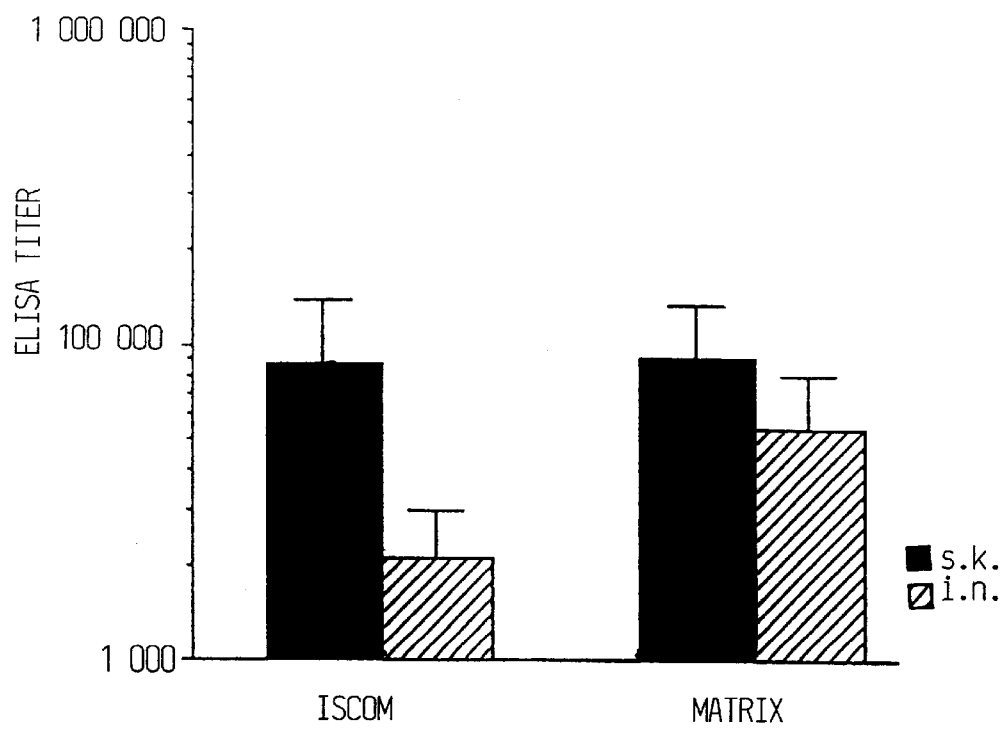

FIGS. 5A and 5B are bar graphs of the same kind as FIGS. 4A and 4B. Mice were immunized subcutaneously with 2 μg rCTB (solid bar) or intranasally with 4 μg rCTB (diagonal bar). FIG. 5 shows serum antibody titers 5 weeks after the first immunization while FIG. 5B shows the titer 6 weeks after the second immunization. The interval between the immunizations was 6 weeks.

Figure 6A:
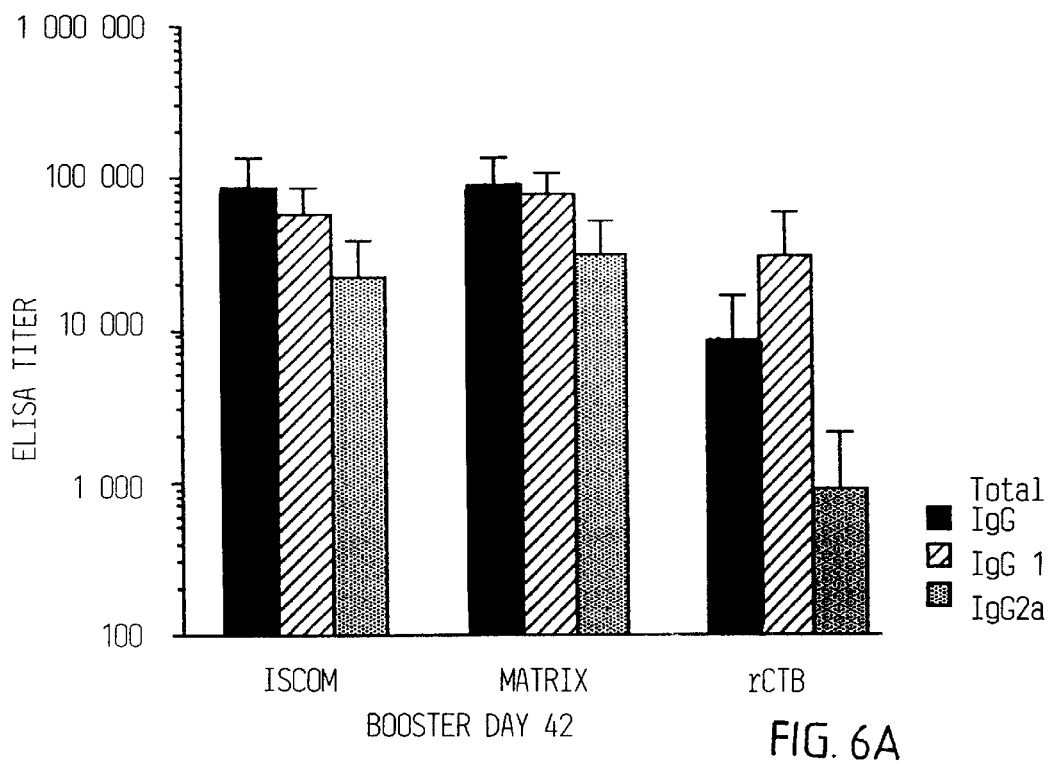
Figure 6B:
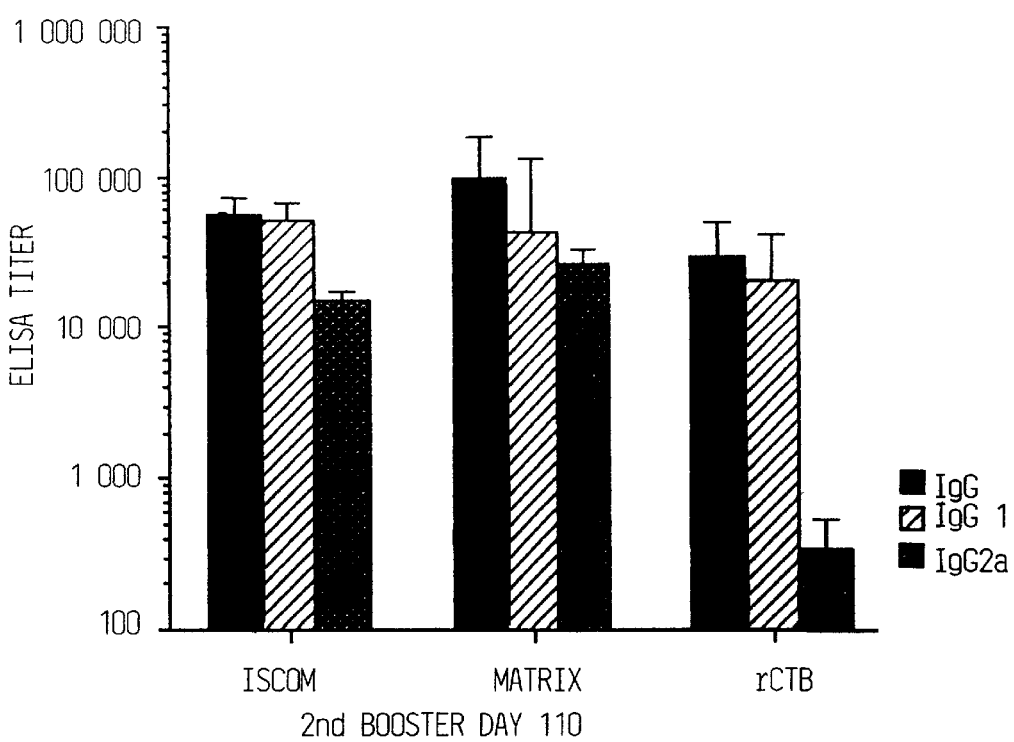

FIG. 6 shows the antibody titers after different immunizations. rCTB mixed with matrix and rCTB bound in iscom evoke, after subcutaneous immunization, serum antibodies of subclass. IgG2a and IgG1 unlike rCTB, which almost only evokes IgG1. FIG. 6A shows the result 14 days after the first booster immunization on day 42 while FIG. 6B shows the values 4 days after the second booster immunization on day 110.

Figure 7:
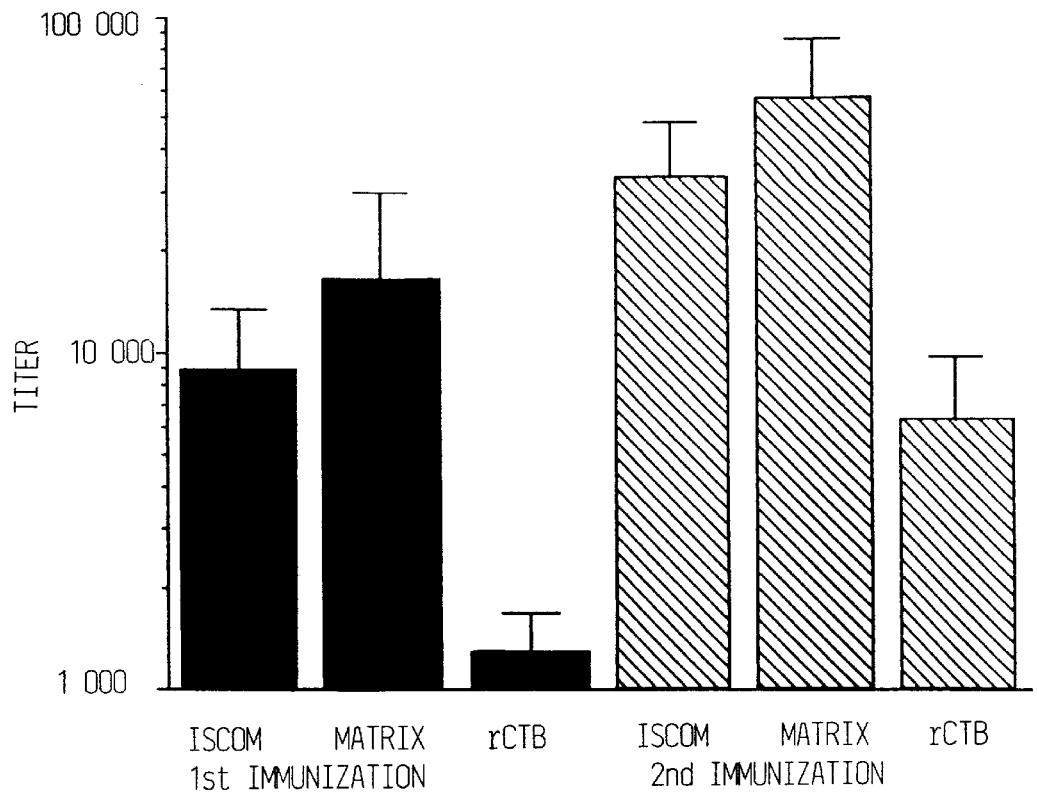

FIG. 7 shows the result after subcutaneous immunization of mice with rCTB bound to matrix, rCTB mixed with matrix, and only rCTB. The serum antibody response 14 days after the first immunization and 14 days after the second immunization are shown. The interval between the immunizations was 42 days.

Figure 8:
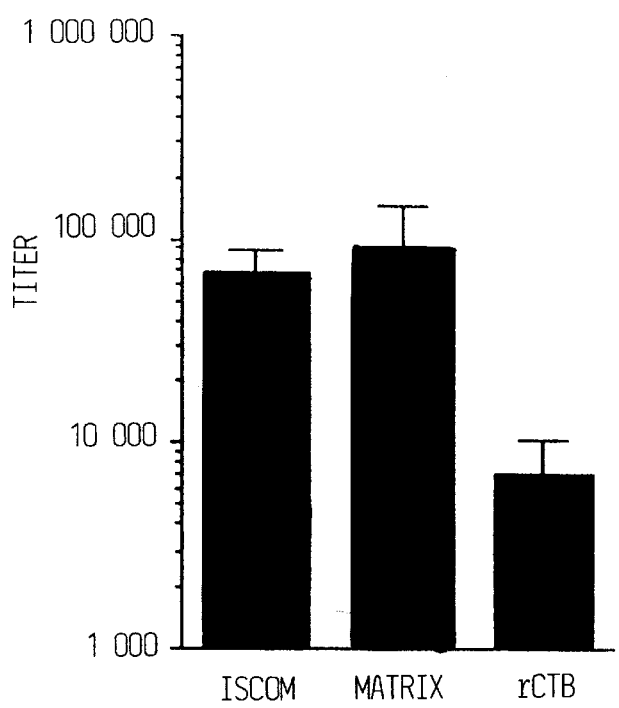

FIG. 8 shows the memory cell response after the second booster on day 180 for the same immunization as in FIG. 6. Four days after the booster dose, serum samples for antibody determination were taken.

The invention will now be described more closely regarding the following procedure examples.

EXAMPLE 1

Incorporating GM1 and rCTB in Iscoms

The cholera toxin (CT) is an effective adjuvant especially in local mucosal immunization. Even the cholera toxin's B subunit (CTB) is classified as an adjuvant because of its target-seeking qualities in local immunization, but this activity is thus limited to a guiding function for the antigen to the lymphatic cells of the intestines. If CTB is bound to iscom matrix or is incorporated in iscom, a formulation that enhances the immune response is obtained, and is effective in local and parental immunizations. This effect is interesting in connection with vaccines against cholera and in choosing adjuvant for the other antigens for local mucosal or parenteral immunizations. The recombinant cholera toxin, subunit B (rCTB) EP 0 368 819) is mixed with different preparations with:

MEGA-10(Bachem P1000 Decanoyl-n-methylglucamide), 20 weight-% in $H_2O$;

Phosphatidylcholin (PC) (Sigma P 5763), 10 mg/ml dissolved in 20 weight-% MEGA-10 in $H_2O$.

Cholesterol (C) (Sigma C 8667), 10 mg/ml dissolved in 20 weight-% MEGA-10 in $H_2O$;

GM1 (Sigma G7641), 10 mg/ml dissolved in 20 weight-% MEGA-10 in $H_2O$;

Phosphatidylethanolamine (PE) (Sigma P2768), 10 mg/ml dissolved in 20 weight-% MEGA-10 in $H_2O$;

Quil A (Spikoside, Iscotec, Luleå), 100 mg/ml in $H_2O$;

rCTB, 5 mg/ml in a buffer solution with 0.05 M TRIS (pH 7.5), 0.2 M NaCl 0.0001 M Na2 EDTA, 0.003 M NaN3;

Phosphatidylcholin was mixed with cholesterol plus trace amounts of radioactive cholesterol ($^3$H-cholesterol Amersham) in the proportion 1:1 (100 mg av each lipid in 10 ml 20% MEGA-10) and with varying amounts of GM1 from 1 μg to 7.5 μg (1 μg 1.7 μg, 2.5 μg, 4 μg, 5 μg, 7.5 μg) in 1.0 ml PBS (phosphate-buffered physiological NaCl-solution), pH 7.2.

Into 1 ml of the six different variants of phosphatidylcholin/cholesterol-GM1-solution, Quil A was added, to a final concentration of 0.2%. The mixtures were sonicated in a Sonorex TK 52 2×15 min. and were left at room temperature (RT) for 1 hour. Then the mixtures were dialyzed against PBS, first for twenty-four hours in RT and then for twenty-four hours in a cold-room (+4° C.). That matrix was formed could be seen by electron microscopy. Into each of the six different matrix variants, which differed regarding GM1 content, 100 μg rCTB were added. The mixtures were left for two hours in RT. The matrix particles with associated rCTB, ie iscom, were purified by centrifugation in a 10–50% sucrose gradient in PBS for 18 hours in a TST 41.14-rotor (Kontron) at 39 000 rpm in 10° C. The gradient was collected in 16 to 18 fractions. The fractions were analyzed in reference to rCTB using the protein-determination method according to Bradford (Bradford, Analyt. Biochem., 72, 1976, 248–254) and was determined cholorimetrically at 595 nm, and in reference to lipids through detection of $^3$H-cholesterol, and electron microscopy to study the presence of possible matrix or iscom structures. FIG. 1 shows free fractions 12–14. FIGS. 2 and 3 show the lipid (■) and rCTB (□) amounts in the fractions when the ratio of rCTB:GM1 is 13:1 (FIG. 2), where iscom with rCTB exists in the fractions 6–9, or 100:1 (FIG. 3), where non-incorporated rCTB lies higher up in the gradient, ie the fractions 10–12.

Result

The greatest relative amount (weight) of rCTB that was completely incorporated in the GM1 matrix, ie the iscom, was 13 times higher than the amount of GM1 (FIG. 2). In several other experiments, we have seen the same ratio. If a higher amount of rCTB is added, the surplus rCTB is found higher up on the gradient unassociated with $^3$H cholesterol, which shows that this rCTB is not incorporated. If a smaller amount of rCTB is added, aggregates are formed through cross-linking because rCTB has five possible binding sites to GM1. Matrix with associated rCTB, ie iscom, is to be found in the fractions 6–9 (FIG. 2). Similar results are achieved with phosphatidylethanol-amine in matrix or iscom instead of phosphatidylcholin (results not presented).

Conclusion rCTB can effectively be bound to matrix that contains the glycolipid GM1. An addition of an appropriate amount of GM1 during the matrix preparation implies an efficient procedure method.

EXAMPLE 2

In this example, it is shown that rCTB incorporated in iscom evokes a higher antibody response than free rCTB.

GM1 matrix was prepared in the same way as in example 1. Phosphatidylcholesterol and GM1 (PC/C/GM1 and Quil A) in the proportion of 1:1:0.25:5 was mixed with MEGA-10 (final concentration: 2%). The mixture was dialyzed in the same way as in example 1. rCTB was added in an amount (weight) that was 13 times higher than the amount of GM1. In the same way as in example 1, formed complex was analyzed with EM and sucrose gradient centrifugation. Gradient fractions were analyzed as in example 1 regarding cholesterol and protein (rCTB). Iscoms with incorporated rCTB were thereafter saved for use in immunization experiments.

Six groups of eight mice each were immunized subcutaneously with 2 g rCTB or with 4 g rCTB intranasally on two occasions within a six week interval (see FIGS. 4A and 4B). rCTB was present either in a free form, ie mixed with matrix without GM1, or bounded to matrix via GM1. Two variants of GM1 matrix according to the above were used in the weight proportion 13:1 or 25:1 (rCTB:GM1 depending on weight), ie saturated or overly saturated in regards to the proportion rCTB/GM1.

Group A Free rCTB, 2 μg rCTB inj. s. c. 0 μg Quil A

Group B Free rCTB, 4 μg rCTB inj. i. n. 0 μg Quil A

Group C Iscom; 2 μg rCTB (13×GM1) inj. s. c. 3 μg Quil A

Group D Iscom; 4 μg rCTB (13×GM1) inj. i. n. 6.1 μg Quil A

Group E Iscom; 2 μg rCTB (25×GM1) inj. i. n. 1.6 μg Quil A

Group F Iscom; 4 μg rCTB (25×GM1) inj. i. n. 3.2 μg Quil A

The antibody titers in serum were measured using ELISA at different times according to FIGS. 4A and 4B.

In the ELISA test, the ELISA plates (Nunc, Roskilde, Denmark) were incubated with a 50 mM carbonate buffer, pH 9.5, containing 2 μg rCTB/ml. Serum samples from the mice were diluted in series. The ELISA plates were treated with the diluted serum solutions. Bound mice antibodies were detected with peroxidase-conjugated rabbit-anti-mouse conjugate (Dakopatts) and as a substrate. TMB, $H_2O_2$ (EC diagnostics, Uppsala) was used.

Result

The results are outlined in FIGS. 4A and 4B, which show serum antibody titers measured in ELISA 5 weeks after the first subcutaneous and intranasal immunizations with rCTB (A) and 6 weeks after the second immunization (B). The interval between immunizations was 6 weeks. rCTB incorporated in iscom in the proportion of 13:1 (rCTB:GM1 (weight)) evoked, after two subcutaneous immunizations with 2 μg rCTB, a titer of 87 000. Iscoms with a rCTB:GM1 ratio of 25:1 evoked titers of 50 000. Corresponding serum antibody titers for two subcutaneous immunizations with free rCTB were 8 600.

After two intranasal immunizations with rCTB in iscom (13:1) (rCTB:GM1) serum titers of 21 000 were obtained, while 25:1 (rCTB:GM1) evoked serum antibody titers of 33 000. Free rCTB evoked, after two intranasal immunizations. ELISA titers in serum of 19 000.

Conclusion rCTB in iscom is, after subcutaneous immunization, more immunogenic than free rCTB, but there was no significant difference after intranasal immunization.

EXAMPLE 3

In this experiment, matrix was used as adjuvant with non-incorporated antigen in subcutaneous and intranasal immunization.

Matrix without GM1 was prepared basically as described in example 1 with the only difference that GM1 was excluded. The weight proportions of phosphatidylcholin/cholesterol/Quillaja were 1:1:5. Lipids were dissolved in 20% MEGA. Dialysis was conducted as in example 1. Matrix was analyzed and characterized as in example 1 using EM and analytical sucrose gradient centrifugation. Matrix with GM1 was prepared as in example 1 and rCTB was incorporated in the proportion 13:1 (rCTB:GM1). When GM1 was excluded from matrix, no biding of rCTB to matrix occurred.

Eight mice per group were immunized subcutaneously with 2 μg rCTB in iscoms or mixed with matrix as adjuvant or intranasally with 4 μg rCTB in iscoms or mixed with matrix as adjuvant. Two immunizations were carried out within a six week interval.

Group C: Iscom: 2 μg rCTB subcutaneously, 3 μg Quil A

Group D: Iscom: 4 μg rCTB intranasally, 6.1 μg Quil A

Group G: Matrix mixed with: 2 μg rCTB subcutaneously, 3.0 μg Quil A

Group H: Matrix mixed with: 4 μg rCTB intranasally, 6.1 μg Quil A

The antibody titers in serum were measured using ELISA and the titers are given as the dilution that gives the absorbence of 1.0.

Results

The results are summarized in FIG. 5, which shows serum antibody response after immunization with 2 μg rCTB administered s. c. or 4 μg rCTB administered i. n. measured in ELISA 5 weeks after the first immunization (A) and 6 weeks after the second immunization (B). The interval between immunizations was 6 weeks. After two subcutaneous immunizations with rCTB mixed with matrix as adjuvant, an average titer of 91,000 was induced, compared to 87,000 for rCTB in iscom form. After two intranasal immunizations, 54,000 was induced for rCTB mixed with matrix, compared to 21,000 for rCTB in iscom.

Conclusion

After subcutaneous immunization, the serum antibody titers induced by rCTB in iscom form were almost as high as that induced by rCTB mixed with matrix as adjuvant. After intranasal immunization, twice as high titers after immunization with rCTB mixed with matrix were induced as with rCTB in iscom form. It is interesting to note that matrix in free form has as strong an adjuvant effect on antibody response as the iscom form of rCTB. In the matrix formula, twice as much Quillaja was included.

Above all, it is surprising that matrix in free form has an adjuvant effect after local mucosal administration with rCTB, which in itself has an adjuvant effect in the form of targeting when immunized through mucous membranes.

EXAMPLE 4

One of the tasks for an adjuvant is to evoke a strong immune response that can be measured as an antibody response or as a cell-mediated immune response. Another of its tasks is to evoke the desired type of immune response, which eg can be read in IgG subclasses that reflect T-helper cell response identified with cytokine production. In this experiment, it is shown that rCTB in free form without adjuvant evoke a serum antibody response that is focussed to subclass IgG. By mixing rCTB with matrix or by incorporating rCTB in iscom, serum antibodies are also evoked against rCTB in the subclass IgG2a, which is associated with a TH1 response.

Eight mice per group (three groups) were immunized twice subcutaneously at a 6-week interval with 2 μg rCTB without adjuvant or with 2 μg rCTB mixed with matrix or with 2 μg rCTB-iscom.

The serum antibody responses were measured using ELISA according to a time schedule that can be seen in FIG. 6. The distribution of serum antibodies in classes and subclasses was analyzed using ELISA by use of class and subclass-specific antisera (Dakoparts, Denmark).

Results

Free rCTB without adjuvant mainly evoked an IgG1 response against rCTB while no antibodies in subclass IgG2a could be found. Both rCTB-iscom and rCTB mixed with matrix evoked both IgG1 and IgG2a antibodies against rCTB (FIG. 6A) 14 days after the first booster immunization, day 42. Even after a second booster on day 110, free rCTB without adjuvant did not evoke an IgG2 response, while iscom and rCTB mixed with matrix gave a clear IgG2 response (FIG. 6B) 4 days after the 2nd booster immunization.

Conclusion

There are differences in quality regarding the serum antibody response in rCTB in free form without adjuvant as compared to rCTB provided with matrix as adjuvant or bound to iscom. Both matrix and iscom with rCTB evoke antibodies against rCTB of subclass IgG2a as well as IgG1, unlike free rCTB, which is only able to evoke IgG1-antibodies.

EXAMPLE 5

The effect of vaccines against infections depends not only on the direct effect that the evoked immune response has, but also on the induced memory cells that are recruited in connection with infections. The memory cell function is especially important a long time after the vaccination, when the evoked immunity will have become low. A strong memory cell response, that can be recruited quickly at the time of infection, is therefore desirable.

Eight mice per group (3 groups) were immunized twice subcutaneously at an 8-week interval with 2 µg rCTB without adjuvant, with rCTB incorporated in iscom, or rCTB mixed with matrix. The antibody response was measured using ELISA, each group was divided into two subgroups of 4 mice each. A second booster immunization was executed on day 180 and blood tests for serum were taken 4 days later.

Results

The results can be seen in FIG. 7. After the first immunization (day 14), the highest immune responses were evoked by rCTB mixed with matrix (17,000) and rCTB iscom (9,000) rCTB without adjuvant induced titers of approximately 1,000. Two weeks after the second immunization (the interval between immunizations was 42 days), mice in all the groups had increased their serum antibody titers appreciably. The highest titers were found in the matrix group (approximately 57,000) and the iscom group (35,000), while the titers for the group that was vaccinated with rCTB without adjuvant had titers of approximately 6,000.

After the third immunization (i.e. the second booster) on day 180, i.e. 140 days after the second immunization, the mice that were immunized with free rCTB had antibody titers of approximately 8,000, i.e. just about the same titers as after the second immunization. Mice that were immunized with iscom or with rCTB mixed with matrix responded after the 3rd immunization on day 180 with increased serum antibody titers for matrix (approx. 90,000) and iscom (approx. 70,000) (FIG. 8). Serum was taken 4 days after the 3rd immunization for antibody tests.

Conclusion

The strong antibody increase in serum in mice that were reimmunized a long time after the earlier immunization (140 days) with rCTB iscom or with rCTB mixed with matrix shows that a strong memory response has been evoked by the previous immunizations. rCTB without adjuvant, however, did not show any immune response that can be boostered after a long time.

EXAMPLE 6 rCTB was preincubated at 20° C. for 1 hour with GM1-containing matrix in proportions that were tested in advance so that preparation (A) should saturate matrix with rCTB, and so that preparation (B) would give an supersaturation so that approx. half the amount of rCTB could not bind to matrix. After incubation, the matrix was purified from unbound rCTB through centrifugation.

Preparations A and B were then used for peroral, intranasal, or intraperitoneal immunization of 8–10-week-old C57/B1 mice. Groups of 3 mice in each group were given 3 doses with a 2-week interval between the doses. Each dose contained 17 µg rCTB and 26 µg Quillaja for peroral immunization, half the dose for intranasal, and a sixth for intraperitoneal immunization.

Three more groups of mice were given peroral, intranasal, and intraperitoneal immunizations, respectively, with corresponding amounts of matrix (not containing GM1) mixed with rCTB.

One week after the third dose, the animals were killed, exsanguinated, and perfused with PBS-heparin whereafter lung tissue was taken from both lungs and crushed, and pieces of the intestinal canal were taken from the upper, middle and lower parts of the small intestine and were crushed. The tissue was frozen at −30° C. and was then thawed and suspended in PBS-1% saponine (1 ml per 1 mg tissue) and was extracted in cold (+4° to 10° C.) over the night. The tissue extract and sera were then titered for specific antibodies against CTB using GM1-ELISA.

The results can be seen in Table 1. It is evident that all of the preparations A–C give high serum antibody responses after intraperitoneal and intranasal immunization and that intranasal immunization with (A) and (B) stimulate good local IgA antibody titers in tissue extract from respiratory tract cells.

TABLE 1

ANTIBODY TITERS IN MICE IN SERUM AND TISSUE EXTRACT AFTER INTRAPERITONEAL (LP): INTRANASAL (IN) OR ORAL IMMUNIZATION WITH B-SUBUNIT (rCTB) FROM THE CHOLERA TOXIN IN ISCOM

|   |    | LUNG |      | INTESTINE |      | SERUM |      |
|---|----|------|------|-----------|------|-------|------|
|   |    | IgA  | IgG  | IgA | IgG | IgA | IgG |
| A | PO | <2   | 15   | 42  | <2  | 35  | 1400 |
|   | IN | 2900 | 20,700 | 21 | 140 | 970 | >400,000 |
|   | IP | <2   | 7000 | 18  | 350 | <2  | 260,000 |
| B | PO | <2   | 14   | 22  | 20  | 10  | 6,800 |
|   | IN | 1550 | 7000 | 240 | 510 | 1420 | >400,000 |
|   | IP | <2   | 220  | 100 | 100 | 10  | 120,000 |
| C | PO | <2   | 76   | 39  | 39  | <2  | 99,000 |
|   | IN | 340  | 5,400 | 28 | 415 | 350 | 380,000 |
|   | IP | —    | 6,700 | — | 450 | —   | >400,000 |
| D | PO | 0    | —    | 30  | N.d. | — | — |
| =CTB | IN | 500 | —   | 50  | N.d. | — | 30,000 |
| E | PO | 20   | 2,100 | 4,300 | 800 | 1,300 | 87,000 |
| = CTB + | IN | 10,000 | 46,000 | 500 | 5,100 | 40,000 | 600,000 |
| CT | IP | N.d. | 2,300 | 100 | 480 | 630 | 79,000 |

3 immunizations, 3 mice per group. Median titers are shown.
Mice were immumzed 3 x
A = PC/C + GM1 + rCTB 13 x (saturated)
B = PC/C + GM1 + rCTB 25x (supersaturated)
C = PC/C − GM1 + rCTB (PC/C and rCTB separate)
D = rCTB
E = rCTB + choleratoxin
Dilution expressed as 1/x is < 5
PO = peroral administration 20 µl (17 µg CTB & QA 26 µg)
IP = intraperitoneal 3 µl
IN = intranasal 10 µl

EXAMPLE 7

This example shows that an iscom containing matrix with GM1 and to which rCTB has been bound and incorporated together with an Ovalbumin (OVA) which has been provided with a lipid tail evokes antibody response against rCTB and against OVA after one intranasal (IN) immunization.

Lipidating OVA

Reagent 1 mg OVA 1 mg phosphatidylethanolamin (PE), with small amounts of $^{14}$C-labelled PE 1.4 mg N-hydroxisulfosuccinimide 38.4 mg 1-ethyl-3-(3-dimethylaminopropyl)-charbodiimid-HCl $H_2O$ to a volume of 2 ml.

The mixture was incubated for 2 hours on a shakeboard in room temperature.

This OVA was incorporated in iscoms with and without GM1, analogously with the method described earlier in example 1. The iscoms were characterized through electron microscopy (EM) and analytic sucrose gradient centrifugation in the same was as in example 1.

In iscom preparation the following ingredients were used:

| Lipidated OVA, 2 ml | 300 µg |
| Cholesterol | 1000 µg |
| Spikoside (Quil A) | 5000 µg |
| $H_2O$ to a volume of 2.15 ml | |

For preparation, see example 1.

When the iscoms were also to contain GM1, the following ingredients were used:

| Lipidated OVA | 300 µg |
| Cholesterol | 1000 µg |
| GM1 | 50 µg |
| Spikoside (Quil A) | 5000 µg |
| Total volume 2.2 ml ($H_2O$). | |

In preparing OVA-rCTB iscoms, OVA-GM1 iscoms were mixed with 13 times higher amounts (weight) rCTB than GM1. The amounts were calculated in the same way as in EP 180 562, example 2.1.

Five groups of eight mice each were immunized intranasally twice with a six-week interval according to the following schedule:

| Group A | OVA (free), 10 µg intranasally |
| Group B | OVA-iscom, 10 µg antigen intranasally |
| Group C | OVA-iscom + rCTB (free), 10 µg of each antigen intranasally |
| Group D | OVA-rCTB iscom, 10 µg of each antigen intranasally |
| Group E | OVA-rCTB iscom, 2 µg of each antigen subcutaneously |
| Group F | OVA free + rCTB free 10 µg of each antigen intranasally |

3 weeks after the first immunization and 2 weeks after the second immunization, serum samples were collected. Lungs were prepared 2 weeks after the first and second immunizations for extraction of IgA antibodies. Antibody titers in serum and lung extract were determined in the same way as in examples 1 and 2.

Results After One Immunization

The mice in group D responded with significant levels of antibody titers against rCTB in serum. Significant antibody titers against rCTB were detected in lung extract. Lower antibody titers were obtained against OVA in both serum and lung extract.

After subcutaneous immunization (group E) approx. the same serum antibody levels against CTB as against OVA were obtained. No antibody response was measured against rCTB or OVA in lung extract.

In the mice in group C, that had been immunized intranasally with OVA-iscoms plus free rCTB, antibody titers against rCTB were measured with ELISA serum antibody titres that were of the same level as those in the mice in group D. No antibody titers against OVA could be measured in serum. In lung extract, significant titers against rCTB were measured, but no or very little antibody response could be measured against OVA.

In the mice in group F moderate antibody titers were obtained in serum and lung extract against rCTB after primary immunization (i. n.) but not against OVA.

In mice in the remaining groups (A, B) no antibody titers against OVA could be measured in serum nor in lung extract.

Results After the Second Immunization

High antibody titers against OVA in serum were measured in the mice in groups D and E, ie the mice that were immunized intranasally or subcutaneously, respectively, with OVA-rCTB iscoms.

In lung extract from the mice in group D, antibody titers against both rCTB and OVA were measured.

No or very low titers were measured in lung extract in mice that were immunized subcutaneously with OVA-rCTB iscoms (group E).

In the mice in group C, high antibody responses against rCTB in serum were measured, but very low serum titers were obtained against OVA. In lung extract antibody titers against rCTB but not against OVA were measured.

In the mice in group B (OVA-iscom) low titers against OVA in both serum and lung extract were measured. Free OVA (group A) evoked no detectable antibody titers, in either serum or lung extract.

After the second immunization several-fold serum antibody increase of titres against rCTB but not against OVA was obtained. After the second immunization, IgA antibody titers against rCTB were measured in the lung that were significant but no antibody response was measured against OVA.

Conclusion

The results show that iscoms containing rCTB as transport (targeting) molecules and OVA as passenger antigen effectively induce antibody response against both rCTB and OVA in lung extract and serum. Only OVA, OVA iscoms (iscoms with only passenger antigen) or free OVA plus rCTB iscoms evoked no or very low antibody response against OVA in serum and lung extract.

We claim:

1. Lipid-containing particles, chosen from iscoms and iscom-matrix, comprising at least one receptor for antigen substances from microorganisms, bacteria toxins, fimbria, adhesins and binding active parts thereof, which receptor has been integrated in the particle, and is chosen from lipid-containing receptors or receptors that are hydrophobic.

2. Lipid-containing particle according to claim 1 composed of iscoms containing at least one glycoside, at least one lipid and at least one hydrophobic protein or peptide-containing antigen, further comprising a lipid-containing receptor.

3. Lipid-containing particle according to claim 1 composed of iscom-matrix containing at least one glycoside and at least one lipid, further comprising a lipid-containing receptor.

4. Lipid-containing particle according to claim 3, containing at least two antigens or one antigen and one target-seeking molecule, wherein one antigen is bound to a receptor-binding molecule.

5. Lipid-containing particles according to claim 1, wherein the receptor molecule is a lipid-containing receptor.

6. Lipid-containing particles according to claim 1, wherein the receptor molecule is the lipid-containing receptor GM1 of the cholera toxin and the antigen is the cholera toxin or a subunit thereof, or immuno-logically closely related proteins including heat-labile enterotoxin from *E. coli*, or its subunit that binds to the receptor.

7. Lipid-containing particles according to claim 1, wherein the receptor molecule is a hydrophobic protein.

8. Lipid-containing particles according to claim 7, wherein the receptor molecule is a glycoprotein or fucosylated blood group antigen.

9. Lipid-containing particles according to claim 7, wherein the receptor molecule is the glycoprotein that binds to head-labile enterotoxin from *E. coli* or a subunit thereof and wherein the antigen is the enterotoxin from *E. coli* or a subunit thereof.

10. Vaccine preparation for prophylaxis or immunotherapy, containing particles according to claim 1.

* * * * *

UNITED STATES PATENT AND TRADEMARK OFFICE
CERTIFICATE OF CORRECTION

PATENT NO. : 6,027,732
DATED : February 22, 2000
INVENTOR(S) : Bror MOREIN et al.

It is certified that error appears in the above-indentified patent and that said Letters Patent is hereby corrected as shown below:

On the title page, insert Item [30] as follows:

-- [30]     Foreign Application Priority Data

February 21, 1996      [SE]     Sweden........9600648-1--.

Signed and Sealed this

Twenty-first Day of November, 2000

Attest:

Q. TODD DICKINSON

Attesting Officer                Director of Patents and Trademarks